(12) United States Patent
Kitagawa

(10) Patent No.: US 7,296,590 B2
(45) Date of Patent: Nov. 20, 2007

(54) LIQUID SUCTION DEVICE

(75) Inventor: Nobuhiro Kitagawa, Akashi (JP)

(73) Assignee: Sysmex Corporation, Kobe-shi (JP)

( * ) Notice: Subject to any disclaimer, the term of this patent is extended or adjusted under 35 U.S.C. 154(b) by 207 days.

(21) Appl. No.: 11/060,770

(22) Filed: Feb. 18, 2005

(65) Prior Publication Data

US 2005/0183774 A1  Aug. 25, 2005

(30) Foreign Application Priority Data

Feb. 25, 2004 (JP) ............................ 2004-050021

(51) Int. Cl.
*F16K 21/18* (2006.01)
(52) U.S. Cl. .................. 137/399; 137/398; 137/588; 222/464.4
(58) Field of Classification Search ............... 137/398, 137/399, 588; 222/464.4, 464.6; 251/210
See application file for complete search history.

(56) References Cited

U.S. PATENT DOCUMENTS

| | | | |
|---|---|---|---|
| 2,656,849 A * | 10/1953 | Deatrick et al. | ............ 137/399 |
| 2,985,423 A * | 5/1961 | Tischler et al. | ............. 251/210 |
| 3,217,761 A | 11/1965 | Shapiro | |
| 4,057,174 A | 11/1977 | Trujillo et al. | |
| 4,068,681 A * | 1/1978 | McNair et al. | ............. 137/588 |
| 4,306,670 A | 12/1981 | Oshikubo et al. | |
| 5,769,284 A * | 6/1998 | Vargas et al. | ............ 222/464.4 |
| 6,955,185 B2 * | 10/2005 | Rauworth et al. | .......... 137/588 |

FOREIGN PATENT DOCUMENTS

DE  44-37 981 A1  4/1995
JP  9-297146 A  11/1997

\* cited by examiner

*Primary Examiner*—Eric Keasel
*Assistant Examiner*—Craig Price
(74) *Attorney, Agent, or Firm*—Birch, Stewart, Kolasch & Birch, LLP

(57) ABSTRACT

A liquid suction device for sucking liquid contained in a vessel is described herein. A liquid retention room having an inflow port and an exhaust port is inserted into the vessel via an opening at an upper part of the vessel and is dipped in the liquid. A suction tube connected to the exhaust port extends from the opening of the vessel. A float member provided in the liquid retention room is enabled to open and close the exhaust port. The liquid is retained in the liquid retention room when the retention room is dipped in the liquid and the float member is floated upward so as to open the exhaust port. The retained liquid is exhausted from the inflow port when the liquid is lessened to reach a predetermined volume or below, and the exhaust port is closed by the float member.

20 Claims, 7 Drawing Sheets

[Fig. 1]
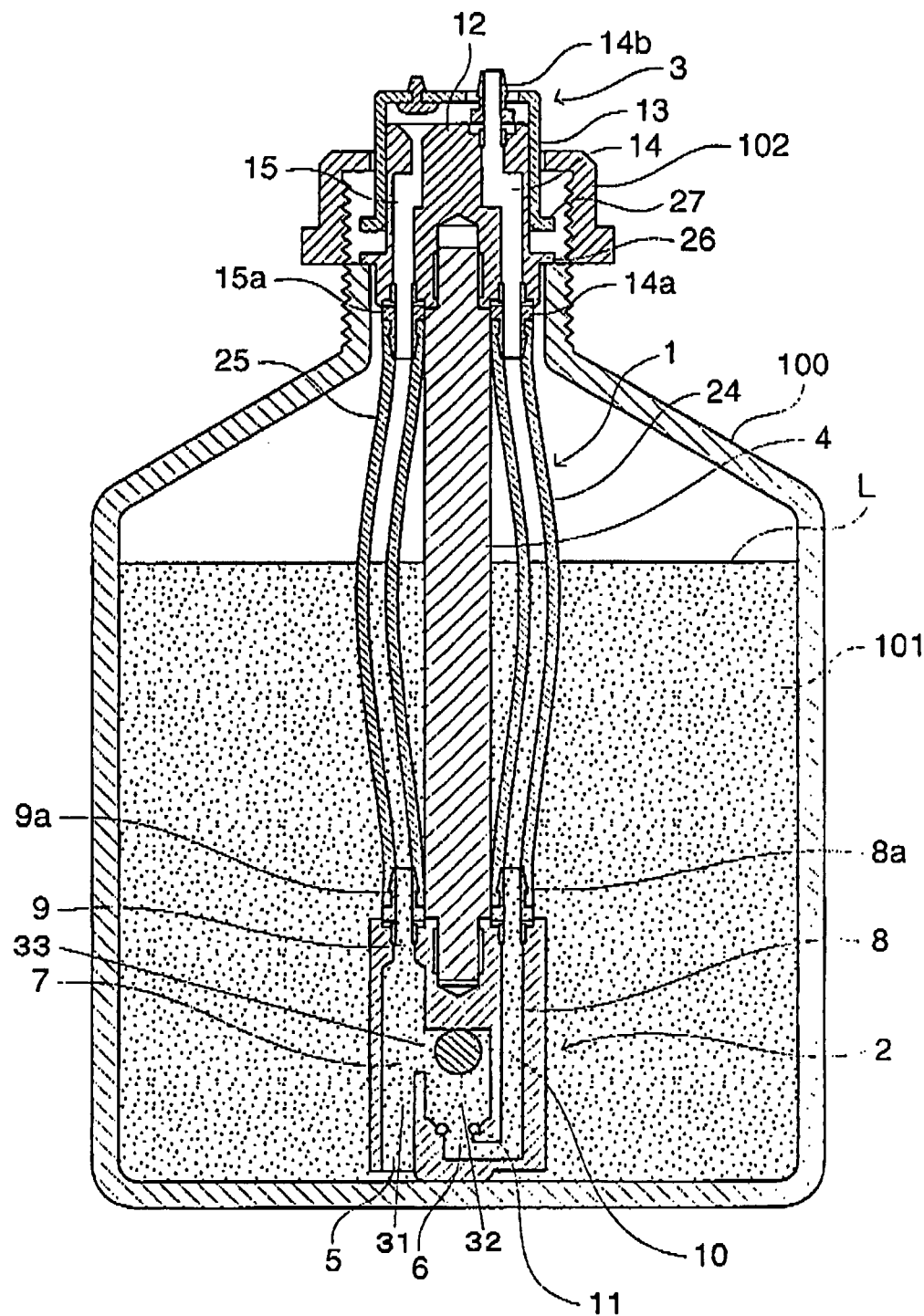

[Fig. 2]
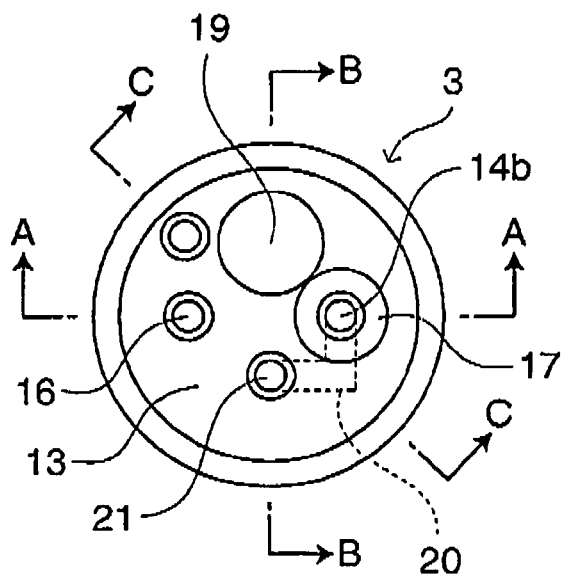
[Fig. 3]
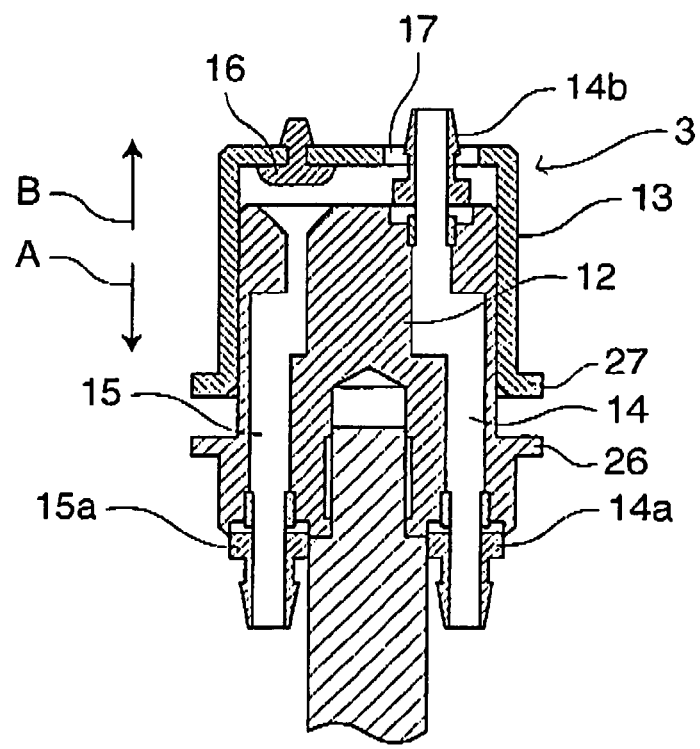

[Fig. 4]
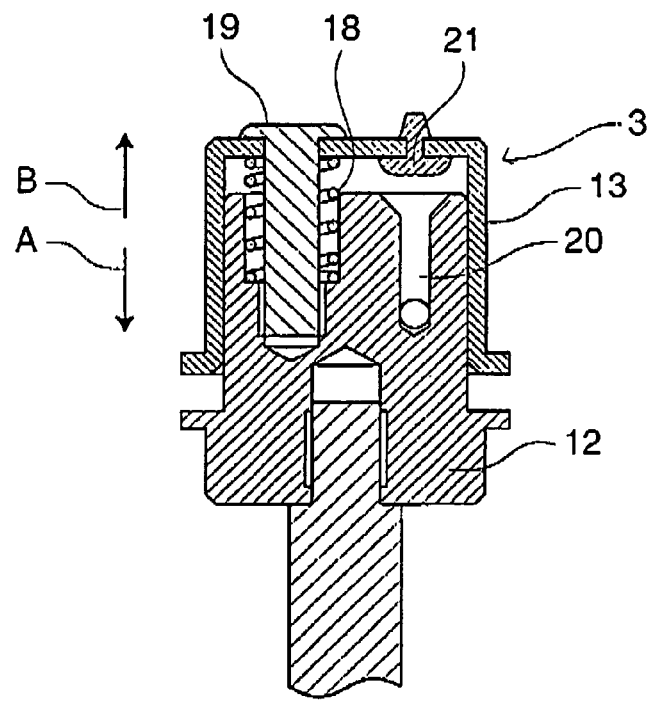
[Fig. 5]
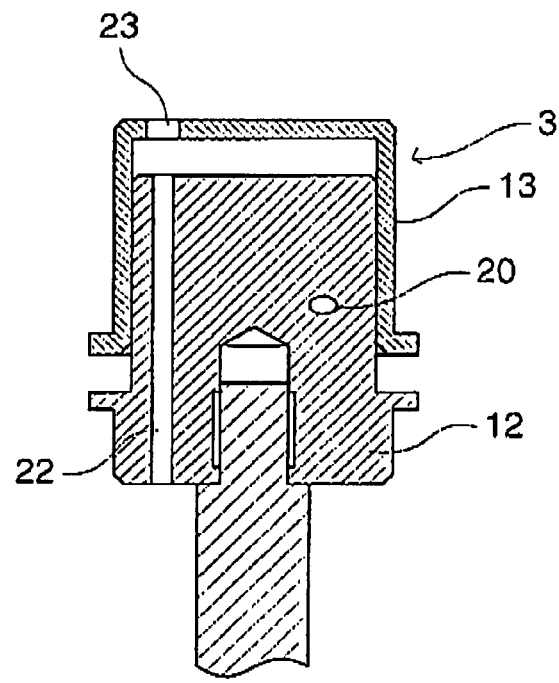

[Fig. 6]
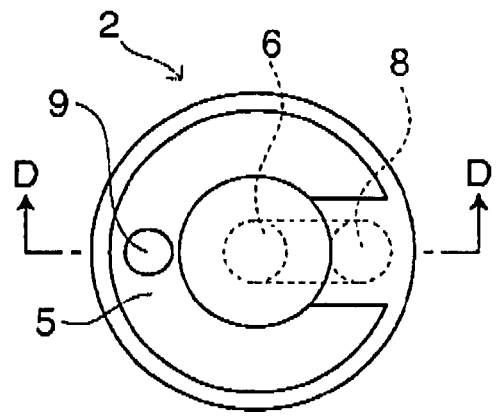
[Fig. 7]
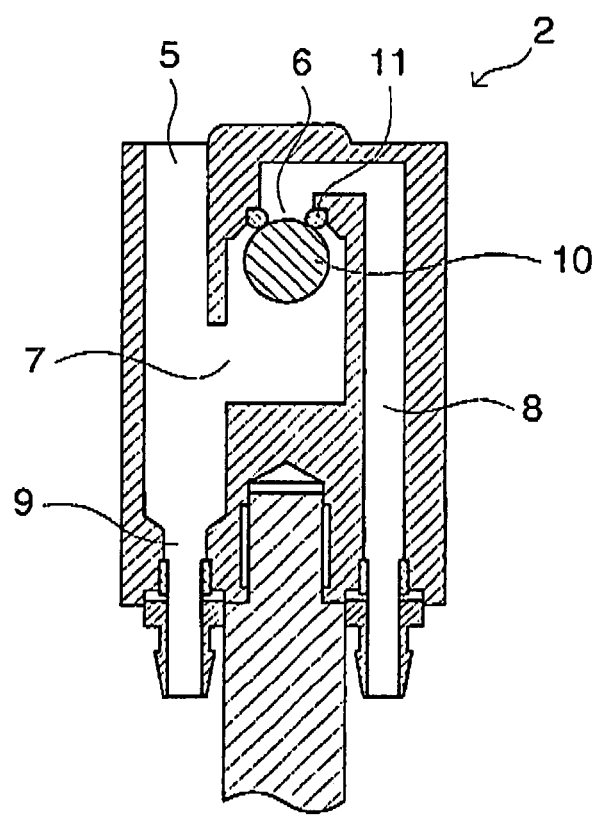

[Fig. 8]
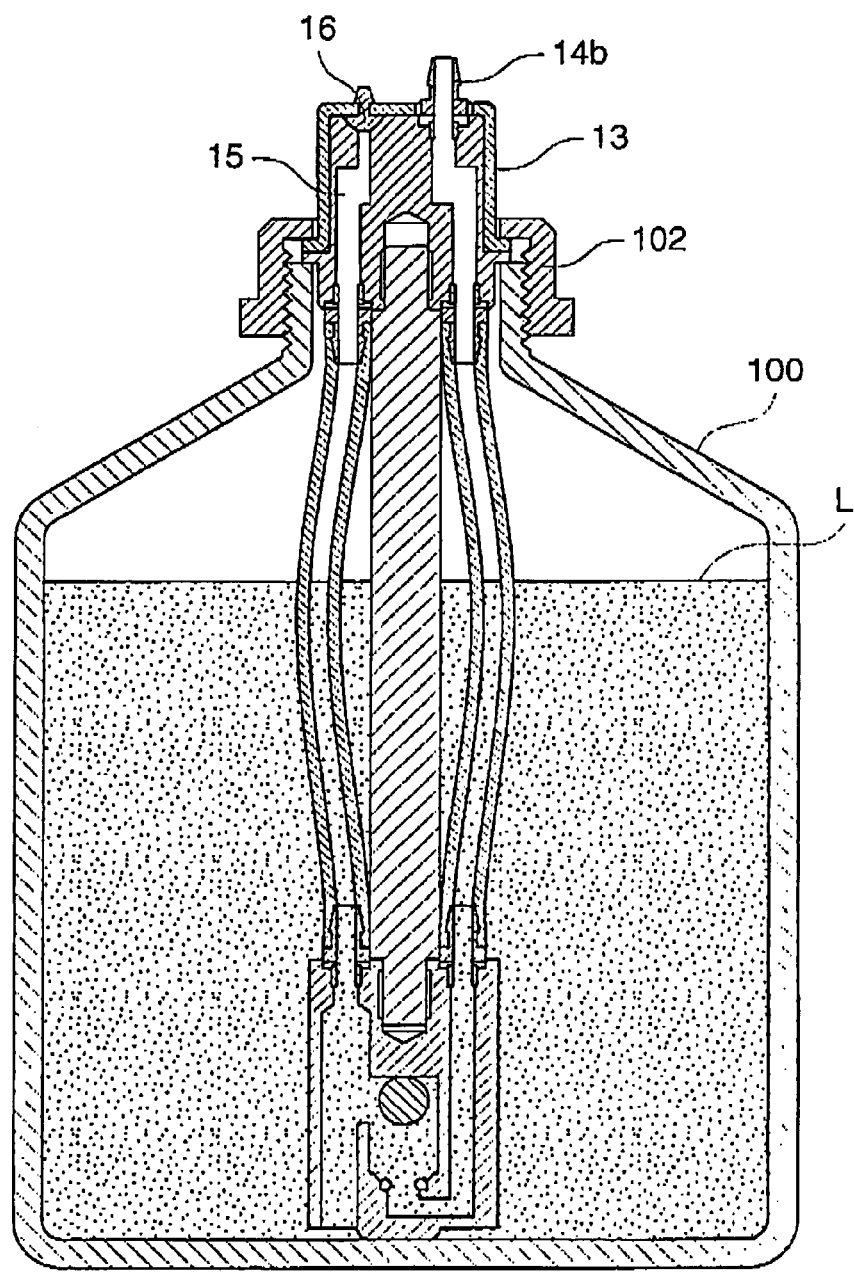

[Fig. 9]
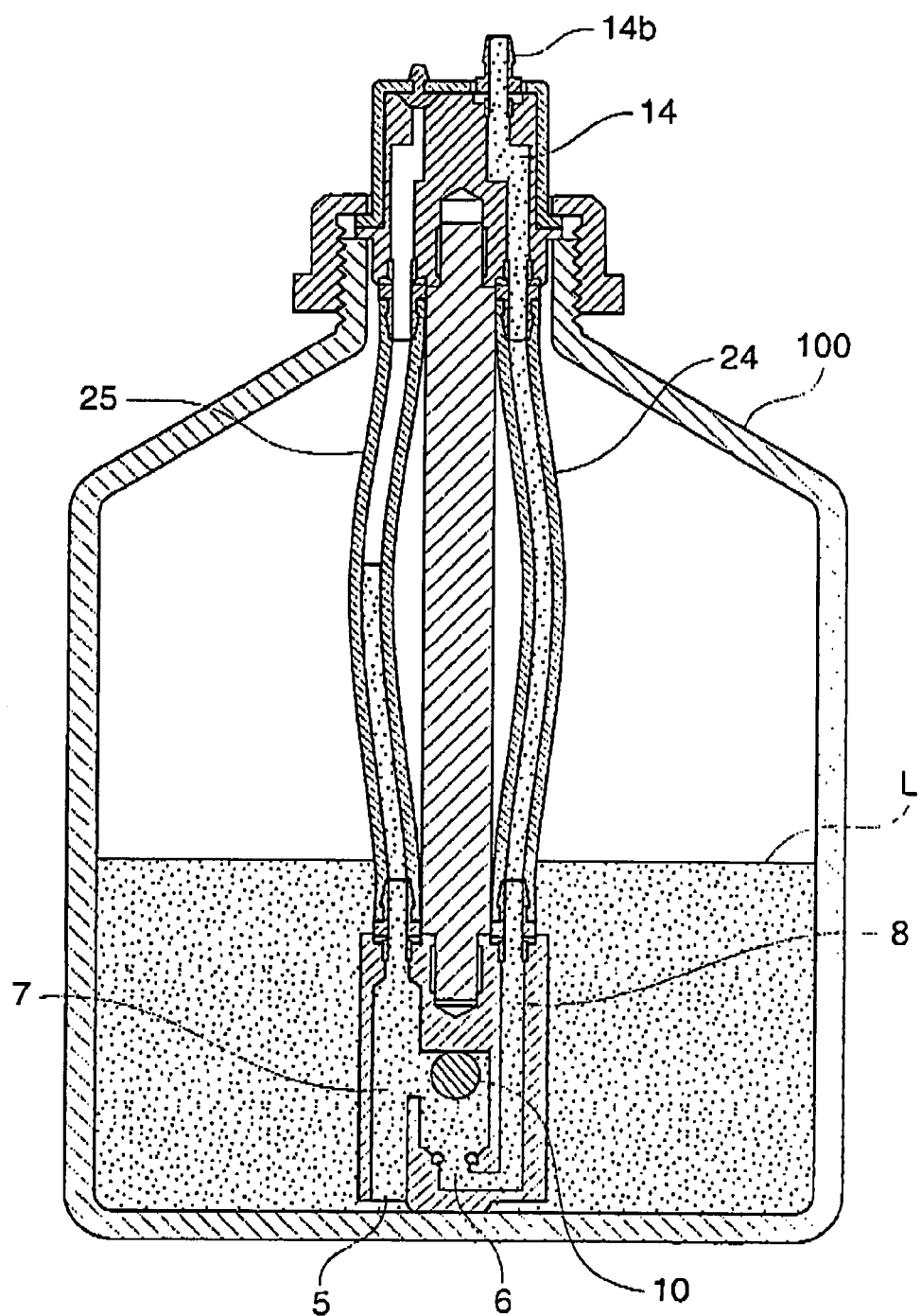

[Fig. 10]
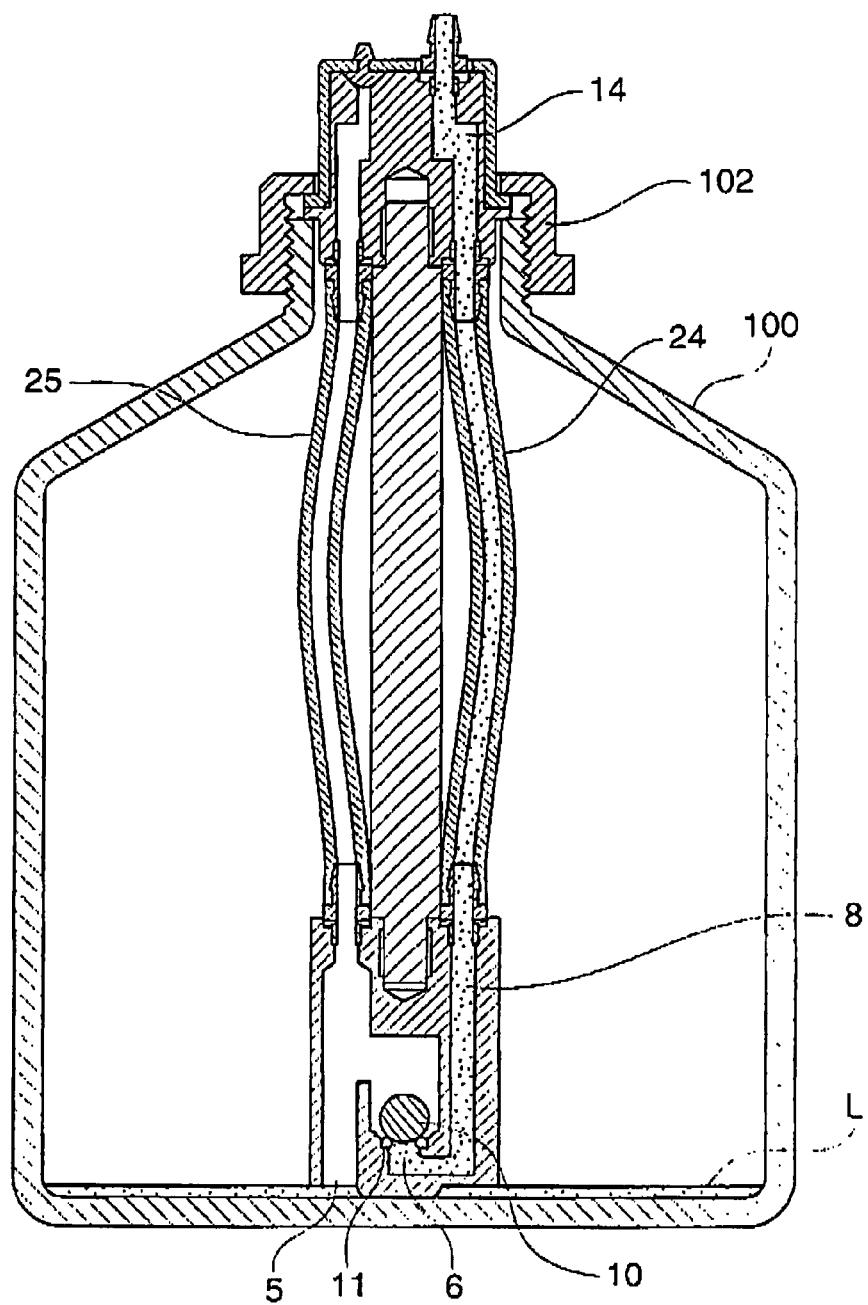

LIQUID SUCTION DEVICE

FIELD OF THE INVENTION

The present invention relates to a liquid suction device for sucking liquid contained in a vessel, more particularly to a liquid suction device used such as a reagent suction device used for sucking a reagent for analysis from a vessel in which the reagent is contained and supplying a clinical testing device with the reagent through a supply tube.

BACKGROUND

In the field of a clinical test, there has been an advancement of automation in the pursuit of an improved measurement precision and also laborsaving. More specifically, clinical testing devices such as a dispensation device for dispensing a certain amount of liquid, a dilution device for diluting a test specimen to a certain ratio, and further, an automatic analyzer in which a process from quantifying the test specimen and dispensing a reagent to a measurement step is fully automated, have been so far developed.

In the foregoing clinical testing devices, a supply tube, such as a pliable tube, is connected to an opening portion of the vessel in which the reagent for analysis is contained, and the reagent sucked from the vessel is supplied to a predetermined spot through the supply tube.

Meanwhile, a suction tube to be inserted into the reagent for analysis is provided in the vessel, the reagent in the vessel is sucked through the suction tube and supplied to the clinical testing device through the supply tube.

As the suction tube, a pliable tube, a hard pipe or a suction tube whose edge is connectively provided with a member having a certain weight and a suction hole for preventing the suction tube from floating onto a liquid surface in the reagent vessel is used.

However, in using the pliable suction pipe or hard suction pipe, or suction tube whose edge is connectively provided with the member having the certain weight and the suction hole, in the case in which the reagent is sucked when a remaining volume of the reagent in the vessel is lessened, air as well as the reagent is inconveniently sucked into the tube, which generated air bubbles in the sucked reagent.

Of the generated air bubbles, those having a large size disappear within a relatively short length of time, while it takes a considerable amount of time before the small and fine air bubbles disappear. Further, when the air bubbles are once generated in the reagent including a surface active agent, it becomes even more difficult for the air bubbles to disappear.

In the foregoing situation, there was a resultant problem that the generated air bubbles were counted as particles in measuring the number of the particles in the measured test specimen by means of a particle counting device, for example, which made it not possible to obtain an accurate number of the particles included in the measured test specimen.

Further, in a device which is designed to obtain a concentration of a measurement object included in the test specimen through the measurement of an absorbance, the small and fine bubbles change the absorbance, which generated another problem that it was not possible to obtain the accurate concentration.

In order to solve the foregoing problems, a liquid suction device (see No. H09-297146 of the Publication of the Unexamined Japanese Patent Applications) comprising a suction pipe dipped in liquid contained in a liquid vessel and a float valve provided in the vicinity of an edge of the suction pipe for gradually closing an opening at the edge of the suction pipe in response to the lowering of a liquid level in the liquid vessel has been proposed.

However, in the recited liquid suction device, the edge of the suction pipe is gradually closed in response to the liquid level, which generates a risk of the air incorporation immediately before the halt of the liquid suction. Therefore, the foregoing method may not be suitably applied to certain types of analyzers and testing devices.

SUMMARY

Therefore, a main object of the present invention is to provide a liquid suction device having a simple constitution and capable of preventing the air incorporation in the liquid suction when the remaining volume of the liquid in the vessel is lessened to reach a certain value.

A liquid suction device for sucking liquid contained in a vessel of a first aspect of the present invention comprises: a liquid retention room inserted into the vessel via an opening at an upper part of the vessel and dipped in the liquid, the liquid retention room having an inflow port and an exhaust port; a suction tube connected to the exhaust port and extending from the opening of the vessel; and a float member provided in the liquid retention room, the float member opening and closing the exhaust port, wherein the liquid is retained in the liquid retention room when the retention room is dipped in the liquid, the float member is floated upward so as to open the exhaust port, the liquid in the vessel is sucked outward via the inflow port, the retention room, the exhaust port and the suction tube, the retained liquid is exhausted from the inflow port when the liquid in the vessel is lessened to reach a predetermined volume or below, and the exhaust port is closed by the float member.

A liquid suction device for sucking liquid contained in a vessel of a second aspect of the present invention comprises: a liquid retention room comprising a first room having an inflow port for inviting inflow of the liquid contained in the vessel and a second room communicated with the first room and having an exhaust port for exhausting the liquid inflow from the inflow port; a suction tube provided so as to communicate with the exhaust port, the suction tube for sucking the liquid contained in the vessel; and a float member housed in the second room.

BRIEF DESCRIPTION OF THE DRAWINGS

FIG. 1 is a longitudinal sectional view of a liquid suction device before the liquid suction device is inserted into and fixed to a liquid vessel.

FIG. 2 is a top view of a base-end member of the liquid suction device.

FIG. 3 is a sectional view taken along A-A line of FIG. 2.

FIG. 4 is a sectional view taken along B-B line of FIG. 2.

FIG. 5 is a sectional view taken along C-C line of FIG. 2.

FIG. 6 is a bottom view of a top-end member of the liquid suction device.

FIG. 7 is a sectional view taken along D-D line of FIG. 6.

FIG. 8 is an illustration of an operation of the liquid suction device.

FIG. 9 is an illustration of the operation of the liquid suction device.

FIG. 10 is an illustration of the operation of the liquid suction device.

DETAILED DESCRIPTION OF THE PREFERRED EMBODIMENT

Hereinafter, the present invention is described in detail based on an embodiment shown in the drawings though the present invention is not limited to the embodiment.

Constitution of Liquid Suction Device

FIG. 1 is a longitudinal sectional view of a liquid suction device and liquid vessel before the liquid suction device is inserted into and fixed to a liquid vessel.

As shown in the drawing, a liquid suction device 1 comprises a top-end member 2 inserted into a liquid vessel 100 via an upper opening thereof and dipped in liquid 101, a base-end member 3 mounted on the upper opening of the liquid vessel 100, and a column-shaped member 4 whose one end is combined with the top-end member 2 by means of screws and another end is combined with the base-end member 3 by means of screws. The top-end member 2, base-end member 3 and column-shaped member 4 are made of polyacetal resin having a chemical-resistant property.

The top-end member 2 comprises a retention room 7 for retaining the liquid 101, an inflow port 5 for inviting the inflow of the liquid 101 into the retention room 7, an exhaust port 6 for exhausting the liquid 101 from the retention room 7, a flow channel 9 for opening the retention room 7 to the atmospheric air, a flow channel 8 for sucking the liquid from the inflow port 5 via the retention room 7 and the exhaust port 6, a float member 10 of a spherical shape provided in the retention room 7 so as to move in vertical directions and having a specific gravity smaller than that of the liquid 101, and an O ring 11 for closing the exhaust port 6 by means of the float member 10. Nipples 8a and 9a are provided in respective end portions of the flow channels 8 and 9. The float member 10 is made of a foaming member using ethylenepropylene rubber which is a material having a specific gravity smaller than that of the liquid. Further, the float member is a spherical body having an outer diameter larger than an opening diameter of the exhaust port so as to open and close the exhaust port.

The retention room 7 comprises a first room 31 comprising the inflow port 5 and a second room 32 comprising the exhaust port 6 communicatingly linked via communicating port 33 to the first room. The float member 10 is housed in the second room.

FIG. 2 is a top view of the base-end member 3. FIG. 3 is a sectional view taken along A-A line of FIG. 2.

As shown in FIG. 3, the base-end member 3 comprises a main body member 12 and a cap member 13 mounted on the main body member 12 from an upper direction so as to slide in directions of arrows A and B. Junction flow channels 14 and 15 are vertically formed in the main body member 12.

Nipples 14a and 14b are connected to both ends of the junction flow channel 14. A nipple 15a is connected to a lower end of the junction flow channel 15. In the cap member 13, an elastic member 16 is provided in a position thereof facing an upper end of the junction flow channel 15, and the elastic member 16 is thereby adapted to close the upper end of the junction flow channel 15 when the cap member 13 moves in the direction of the arrow A.

The cap member 13 has an opening 17 in a position thereof facing the nipple 14b. The nipple 14b is constantly protruded from the cap member 13 via the opening 17, and a suction tube (not shown) from an external device is connected to the nipple 14b.

FIG. 4 is a sectional view taken along B-B line of FIG. 2. As shown in the drawing, the base-end member 3 comprises springs 18 for elastically drawing the cap member 13 from the main body member 12 in a direction of an arrow B and an adjustment bolt 19 for adjusting a distance by which the cap member 13 is drawn away from the main body member 12.

Further, the main body member 12 has a flow channel 20 for opening to the atmospheric air whose one end is open to an upper surface of the main body member 3 and another end is connected to the junction flow channel 14 of FIG. 3. In the cap member 13, an elastic member 21 is disposed so as to face an opening end of the flow channel 20, and the elastic member 21 is thereby adapted to close the opening end of the flow channel 20 when the cap member 13 moves in an direction of an arrow A.

FIG. 5 is a sectional view taken along C-C line of FIG. 2.

As shown in the drawing, the main body member 12 has a vertical through hole 22, the cap member 13 has an opening 23 coaxial with the through hole 22, an internal part of the liquid vessel 100 shown in FIG. 1 is constantly opened to the atmospheric air via the through hole 22 and the opening 23.

FIG. 6 is a bottom view of the base-end member 2 of the liquid suction device. FIG. 7 is a sectional view taken along D-D line of FIG. 6.

As shown in the drawings, the inflow port 5 is formed in such manner as to have an opening area of at least ten times as large as an opening area of the exhaust port 6. Therefore, as described later, the liquid 101 in the retention room 7 is instantly replaced by air via the inflow port 5 when the liquid 101 reaches a certain volume or below so that the float member 10 can immediately close the exhaust port 6.

As shown in FIG. 1, the nipples 14a and 15a of the base-end member 3 are respectively connected to the nipples 8a and 9a of the top-end member 2 by means of pliable tubes 24 and 25. Further, an engaging piece 26 having a flange shape is horizontally protruded from an outer peripheral surface of the main body member 12. The engaging piece 26 is thereby adapted to engage the main body member 12 with an end portion of the opening when the main body member 12 is inserted into the upper opening of the liquid vessel 100. The pliable tubes 24 and 25 are formed from a silicon tube having a chemical-resistant property.

A cap 102 shown in FIG. 1 is an accessory attached to the liquid vessel 100, an upper part of which is opened and closed by means of screws. When the liquid suction device 1 according to the present invention is used, the cap 102 is previously provided with a processed insertion hole. A lower edge of the cap member 13 is provided with an engaging piece 27 protruding outward in a flange manner, which is engaged with an edge part of the hole provided in the cap 102 when the cap 102 is fastened so that the cap member 13 moves downward in the direction of the arrow A (FIG. 4) in response to the fastening operation.

Method of Use

In the foregoing constitution, the suction tube of the external device (for example, clinical testing device), which is not shown, is connected to the nipple 14b of FIG. 1, and the liquid suction device 1 is inserted into the liquid vessel 100 by a user through the hole of the cap 102 attached to the liquid vessel 100. The liquid vessel 100 contains the liquid 101 of a liquid level L. As shown in FIG. 1, an edge of the top-end member 2 contacts a bottom surface of the liquid vessel 101, and the base-end member 3 is accordingly held in the upper opening of the liquid vessel 100. Thus, an edge of the top-end member 2 is formed so as to face the bottom surface of the liquid vessel, and the top-end member 2 is thereby held substantially vertical to the bottom surface. When the top-end member 2 is formed so as to face the bottom surface of the vessel, the inflow port 5 and the exhaust port 6 of the top-end member 2 are also disposed so as to face the bottom surface of the vessel. Further, a clearance for sucking the liquid is formed between the inflow port 5 and the bottom surface of the vessel because the edge of the top-end member 2 is protruded relative to a peripheral part of the inflow port 5.

At this point, the cap 102 is not at all fastened with respect to the screws at the opening of the liquid vessel 100, and the cap member 13 of the base-end member 3 is being lifted in the direction of the arrow B as shown in FIG. 4. Therefore, the junction flow channel 14 (FIG. 1) is opened to the atmospheric air via the flow channel 20 (FIG. 4), and further, the retention room 7 is opened to the atmospheric air via the flow channel 15 (FIG. 1). Accordingly, the liquid 101 flows into the retention room 7 from the inflow port 5 to fill the retention room 7 in accordance with a principle of a communicating tube. The float member 10 rises in response to a buoyancy of the liquid 101 in the retention room 7 and is thereby detached from the exhaust port 6. The liquid 101 rises to a same height as the liquid level L of the liquid 101 in the pliable tubes 24 and 25.

Next, as shown in FIG. 8, when the user fastens the screws to the cap 102, the cap 102 is correspondingly engaged with the engaging piece 27 (FIGS. 1 and 3) so that the cap member 13 is drawn downward. The opening end of the junction flow channel 15 and the opening end of the flow channel 20 (FIG. 4) are respectively closed by means of the elastic members 16 and 21.

Next, when a negative pressure is applied from the external device via the nipple 14b, the liquid 101, as shown in FIG. 9, is sucked into the external device through the inflow port 5, retention room 7, exhaust port 6, flow channel 8, pliable tube 24, junction flow channel 14 and nipple 14b, in response to which the liquid level L is gradually lowered. At this point, the liquid level of the liquid in the pliable tube 25 is maintained at the same height as the liquid level L of FIG. 1 because the junction flow channel 15 is closed.

Then, when the liquid level L in the liquid vessel 100 becomes lower than the inflow port 5 as shown in FIG. 10 to thereby invite the inflow of air, the liquid 101 retained in the pliable tube 25 and the retention room 7 is instantly replaced by the air and thereby escapes from the inflow port 5. At the same time, the float member 10 drops and thereby closes the exhaust port 6.

Therefore, in the case in which the negative pressure from the external device is thereafter continuously applied, the negative pressure serves to make the float member 10 tightly contact the exhaust port 6. Then, the liquid 101 continuously stays in the flow channel 8, pliable tube 24 and junction flow channel 14, which eliminates the possibility of the air being sucked into the external device.

In due course of time, the external device detects that the suction is no longer possible and halts the suction operation. When the user releases the screws of the cap 102 until the state shown in FIG. 1 arrives, the junction flow channel 14 is opened to the atmospheric air. The liquid remaining in the junction flow channel 14, pliable tube 24 and flow channel 8 is correspondingly exhausted into the vessel 100 via the inflow port 5.

The float member 10 in the tight contact with the exhaust port 6 is then released from the exhaust port 6. The user extracts the liquid suction device 1 from the liquid vessel 100 with the external device remaining connected and install the device in a new liquid vessel as shown in FIG. 1. The same suction operation as described so far can be thereby easily repeated.

In the present embodiment, the top-end member is forcibly dipped in the liquid by means of the column-shaped member inserted from the opening of the vessel, however, may be formed from a material having a specific gravity larger than that of the liquid to be thereby dipped in the liquid as a result of its own weight.

In many cases, the liquid is a test specimen such as a hemolytic agent. Therefore, the top-end member is preferably formed from a material having a chemical-resistant property.

An example of the material having a specific weight substantially larger than that of the liquid and chemical-resistant property usable for the top-end member, which can be dipped by its own weight, is preferably stainless steel (SUS316).

In the present embodiment, the polyacetal resin is used as the top-end member, however, chloroethylene resin may be alternatively used.

In the present embodiment, the foaming member using ethylenepropylene rubber is used as the float member provided in the retention room and serving to open and close the exhaust port. However, a foaming member using silicon rubber may be alternatively used.

In the present embodiment, the silicon tube is used as the suction tube connected to the exhaust port and extending from the opening of the vessel. However, a pliable tube such as a urethane tube or a Teflon (registered trade mark) tube or a hard pipe such as a chloroethylene pipe or a stainless pipe may be alternatively used.

In the present embodiment, the pliable tube is used as the suction tube connected to the exhaust port and extending from the opening of the vessel. However, the suction tube may be provided in the column-shaped member.

What is claimed is:

1. A liquid suction device designed to for sucking liquid contained in a vessel and, comprising:
    a liquid retention room inserted into the vessel via an opening at an upper part of the vessel and dipped in the liquid, the liquid retention room having an inflow port and an exhaust port;
    a suction tube connected to the exhaust port and extending from the opening of the vessel; and
    a float member provided in the liquid retention room, the float member opening and closing the exhaust port,
    wherein the liquid is retained in the liquid retention room when the retention room is dipped in the liquid, the float member is floated upward so as to open the exhaust port, the liquid in the vessel is sucked outward via the inflow port, the liquid retention room, the exhaust port and the suction tube, the retained liquid is exhausted from the inflow port when the liquid in the vessel is lessened to reach a predetermined volume or below, and the exhaust port is closed by means of the float member; and
    a base-end member having first and second openings to atmospheric air and mounted on the opening of the vessel;
    a first opening and closing means and a second opening and closing means for respectively opening and closing the first and the second atmospheric-air openings.

2. A liquid suction device as claimed in claim 1, wherein the retention room comprises the inflow port at a position lower than a position of the exhaust port, the retained liquid is exhausted from the inflow port in response to inflow of air from the inflow port resulting from the lessened liquid in the vessel, and the exhaust port is closed by means of the float member.

3. A liquid suction device as claimed in claim 1, wherein the retention room comprises a first room provided with-having the inflow port and a second room communicatingly linked to with the first room and provided withhaving the exhaust port, and the float member is housed in the second room.

4. A liquid suction device as claimed in claim 1, further comprising:
a first communicating portion for communicating the first atmospheric-air opening and the flow channel of the retention room;
a second communicating portion for communicating the second atmospheric-air opening and the suction tube.

5. A liquid suction device as claimed in claim 4, wherein the first and the second atmospheric-air openings are opened by means of the first opening and closing means and the second opening and closing means when the retention room is dipped in the liquid and closed by means of the first opening and closing means and the second opening and closing means when the liquid in the vessel is sucked outward via the suction tube.

6. A liquid suction device as claimed in claim 1, wherein the float member is formed from a spherical body having an outer diameter larger than an opening diameter of the exhaust port.

7. A liquid suction device as claimed in claim 1, wherein the float member is made of a material having a specific gravity smaller than a specific gravity of the liquid.

8. A liquid suction device as claimed in claim 7, wherein the float member is made of foaming ethylenepropylene rubber or foaming silicon rubber.

9. A liquid suction device as claimed in claim 1, wherein an opening area of the inflow port is larger than an opening area of the exhaust port.

10. A liquid suction device as claimed in claim 9, wherein the inflow port has an opening area at least ten times as large as an opening area of the exhaust port.

11. A liquid suction device designed for sucking liquid contained in a vessel and, comprising:
a liquid retention room comprising a first room having an inflow port for inviting inflow of the liquid contained in the vessel and a second room communicatingly linked to with the first room and having an exhaust port for exhausting the liquid inflow from the inflow port;
a suction tube provided so as to communicate with the exhaust port, the suction tube for sucking the liquid contained in the vessel; and
a float member housed in the second room,
a base-end member having first and second openings to atmospheric air and mounted on the opening of the vessel;
a first opening and closing means and a second opening and closing means for respectively opening and closing the first and the second atmospheric-air openings.

12. A liquid suction device as claimed in claim 11, wherein
the float member is formed from a spherical body having an outer diameter larger than an opening diameter of the exhaust port.

13. A liquid suction device as claimed in claim 11, wherein
the float member is made of a material having a specific gravity smaller than a specific gravity of the liquid.

14. A liquid suction device as claimed in claim 13, wherein
the float member is made of foaming ethylenepropylene rubber or foaming silicon rubber.

15. A liquid suction device as claimed in claim 11, wherein
an opening area of the inflow port is larger than an opening area of the exhaust port.

16. A liquid suction device as claimed in claim 15, wherein
the inflow port has an opening area at least ten times as large as an opening area of the exhaust port.

17. A liquid suction device as claimed in claim 11, wherein
the inflow port is disposed at a position lower than a position of the exhaust port.

18. A liquid suction device as claimed in claim 11, further comprising:
a partition wall for dividing the first room and the second room, the partition wall being provided with a communicating port communicatingly linked to with the first room and the second room at an upper part thereof.

19. A liquid suction device as claimed in claim 18, wherein
the communicating port is disposed at a position higher than a position of the inflow port.

20. A liquid suction device as claimed in claim 18, wherein
the exhaust port is disposed at a position higher than a position of the inflow port and a position lower than a position of the communicating port.

* * * * *